United States Patent [19]

Krumeich et al.

[11] Patent Number: 4,865,033

[45] Date of Patent: Sep. 12, 1989

[54] DEVICE FOR HOLDING A CORNEA TAKEN FROM A DONATED EYE

[76] Inventors: Jorg H. Krumeich, Propost-Hellmich-Promenade 28, 4630 Bochum 6, Fed. Rep. of Germany; Lee Nordan, Scripps Memorial Hospital, 9834 Genessee Ave., Suite 209, Lajolla, Calif. 92037

[21] Appl. No.: 83,510

[22] Filed: Aug. 7, 1987

[30] Foreign Application Priority Data

Aug. 8, 1986 [DE] Fed. Rep. of Germany ....... 3626971

[51] Int. Cl.$^4$ ............................................. A61B 17/00
[52] U.S. Cl. .................................... 128/346; 128/305
[58] Field of Search ................ 128/303 R, 305, 305.1, 128/310, 346, 349; 206/363, 370, 438, 5.1; 623/4–6; 215/10, 276; 403/328; 269/20; 248/509

[56] References Cited

U.S. PATENT DOCUMENTS

| | | | |
|---|---|---|---|
| 3,421,648 | 1/1969 | Giessler et al. | 215/276 |
| 3,827,820 | 8/1974 | Hoffman | 403/328 |
| 4,077,411 | 3/1978 | Ward | 128/346 |
| 4,660,556 | 4/1987 | Swinger | 128/305 |

*Primary Examiner*—Michael H. Thaler
*Assistant Examiner*—William Lewis
*Attorney, Agent, or Firm*—Clifford A. Poff

[57] ABSTRACT

The device by means of which a cornea taken from a donor eye is held for processing. The cornea is placed on a round substrate having a central opening. The edge of the cornea is pressed by an annular retaining ring against the substrate. A cavity between the substrate and the pressed cornea is filled with a fluid medium introduced through a central bore in the substrate under a predetermined pressure. The upper end of a base is formed with external threads and, has a central recess for inserting a cylindrical bearing member formed with a central bore. The bearing member is provided with a bevelled upper edge against which the cornea for processing is pressed by a clamping ring whose inner opening tightly clamps the edge of the cornea against the upper edge of the bearing member. The required contact pressure is produced by screwing a tension ring on to external threads on the base. The tension ring acts on the surface of the clamping ring. The central opening of the base can be connected to a source of pressure medium at an adjustable pressure. The pressure medium can be air or a hydraulic fluid.

22 Claims, 4 Drawing Sheets

DEVICE FOR HOLDING A CORNEA TAKEN FROM A DONATED EYE

BACKGROUND OF THE INVENTION

1. Field of the Invention

This invention relates to a device by means of which a cornea taken from a donated eye is held for processing; the cornea being placed on a round substrate having a central opening. The outer edge of the cornea is pressed against the substrate by an annular retaining means. A cavity between the substrate and the cornea is established by filling of a pressure medium which is introduced in the central bore to the cavity.

2. Description of the Prior Art

Disclosed in U.S. Pat. No. 4,077,411 is a device to hold cornea tissue while a trephine cut is made by boring through the cornea of a donated eye. The device comprises a plastic body having a convex surface on which the donated cornea is placed and pressed against the convex surface by an annular disc, using tension springs. A liquid cushion is provided between the cornea and the convex surface of the plastic body to prevent damage to the endothelium layer. The liquid cushion is formed by liquid supplied through a central bore in the plastic body. This device is designed exclusively for perforating keratoplasty and for removing lamellar grafts which are unsuitable for refractive surgery on the cornea, i.e. for changing refractive power of the cornea.

It is known in the art to transplant a cornea by using cornea tissue taken from a donated eye. A distinction is made in this art between perforating keratoplasty and lamellar keratoplasty. In perforating keratoplasty, a cornea disc to be transplanted is obtained by a vertical punching-out of the cornea such as can be obtained by trephine cut. The total thickness of cornea disc is the same as the thickness of the cornea. In lamellar keraloplasty, a horizontal cut across the cornea is made to obtain a layer of cornea which comprises the transplant used for altering the refractive power of the cornea.

In order to obtain a disc of cornea from the donate tissue, the slice of donated cornea is usually placed on a concave substrate so that the top surface of the cornea slice, i.e, the epithelium, confronts the substrate and the inner surface or endothelium is upward and exposed above. The disc of cornea for transplanting is pierced or punched out by using a trepan, i.e. a round knife. A similar disc is removed, likewise by trepanning, from the recipient, i.e., the patient. One disadvantage of the known method used for obtaining cornea discs by perforation, is that during the trepanning operation the donated cornea rests on a substrate which is hard or does not have variable elasticity, so that in the supported condition the cornea will inevitably be completely deformed from the contour of the cornea during the trepanning operation on the patient's eye. It is therefore impossible to obtain identical trepanned disc of cornea, as is necessary for optimum perforating keratoplasty. One reason is that the pressure of the eye varies from patient to patient and because every oblique trepanning operation results in an oval cut and consequently an oval recess in the cornea. Every change in pressure during the trepanning process inevitably results in a change in the diameter of the removed cornea disc. Differences in pressure when trepanning a patient's eye result in relatively severe buckling of the cornea disc in the inner curve of the trepan.

In the known device, where the epithelium of the donated cornea rests downwards on the substrate, differences in deformability result in differences of shape relative to the cornea tissue taken by trepanning from the patient's eye.

An apparatus is disclosed in U.S. patent application Ser. No. 712,249, filed Mar. 15, 1985, and the corresponding West German patent application DE 3409798 for holding a disc of cornea taken from a human eye. The apparatus comprises plunger like moldings which are interchangeably supported in a recess provided in a support member. The support surface of the molding is concave or convex with a predetermined curvature and gas pervious openings communicate with an evacuation chamber so that a corneal disc can be sucked against the corneal support surface by a negative pressure. A pressure ring engages the edge of the corneal disc for clamping it between the pressure ring and molding. A guideway for a transversely-movable cutting device is adjustable relative to the molding. The apparatus is not used for holding a cornea taken from a donated eye, but for holding a lamellar slice of cornea which is taken from the human eye for processing so as to alter the refractive power, using the fixing device, and finally the altered lamanar slice is inserted in the patient's cornea. In order to secure the slice of cornea for processing, its outer edge is bent about the edge of the surface of the bearing member and held by the inner edge of the thrust collar in the space between the collar and the molding member and against the wall of the molding member.

SUMMARY OF THE PRESENT INVENTION

An object of the present invention is to provide a device for holding the cornea taken from a donated eye, so that it is possible, using a cutting device such as a trepan or microkeratome, to obtain a cornea transplant for perforation or a lamellar slice of cornea under the same conditions as when the correspondingly shaped slices of cornea were removed from the patient's eye. This problem cannot be solved by the known devices.

According to one embodiment of the present invention, there is provided a device to hold a cornea taken from an eye for processing, the device including the combination of a base including an upstanding base extension having a central bore and an externally threaded section, a bearing member including a cornea support area and a central cylindrical bore supported by the upstanding base extension, a clamping ring including means for preventing rotation thereof while loosely resting about said bearing member for pressing a cornea for processing against said bearing member, a tension ring threadedly engaged with the externally threaded section of said base for pressing the clamping ring against a part of the cornea while supported by the bearing member, and means for delivering a pressure medium to the central bore of the base.

Advantageously, the upper surface of the centrally bored bearing member is concave and extends from the central bore to a bevelled edge. According to another feature of the invention, the clamping ring is prevented from rotation relative to the bottom part by being provided with downwardly extending pins uniformly distributed over the periphery of the clamping ring. When the clamping ring is placed on the edge of the bearing member, the pins engage in bores formed in the upstanding base section.

It has also been found advantageous to provide the edge of the inner opening of the clamping ring, which clamps the cornea against the bevelled edge of the bearing member, is provided with gripper teeth or constructed with sharp member sections, so that as the cornea is clamped by screwing on the tension ring, the teeth engage in the upstanding base section and prevent the clamping ring from rotating or shifting.

According to the invention the peripheral region of the tension ring is formed with diametrically opposite threaded bores for screwing in threaded bolts having ends projecting downward from the edge of the clamping ring and adapted to be brought to abut against an annular flange on the base section.

The main function of the threaded bolts is to secure the screwed-on tension ring in position and, to prevent movement while a clamped cornea is being processed. In order to remove lamellar slices of cornea, the invention provides one or more discs which can fit into the central recess in the upstanding base section and rest on the bottom of the recess. It is thus possible to vary the vertical position of the bearing member, which is disposed above them, and thus obtain lamellar slices of cornea of varying diameter. Advantageously the tension ring includes a guide track for a microkeratome. According to the present invention, the source of pressure medium can be a syringe, which is tightly connected to the socket on the base. The pressure medium can be air or a hydraulic fluid.

In another embodiment of the invention, a device to hold a cornea taken from an eye for processing, the device including the combination of a base including an upper base having conical bearing surface the projected end of fitted on an outer surface area of the upper base part, the clamping sleeve including an outer peripheral flange and a tension ring threadedly engage with the upper base part and engaged with the peripheral flange for pulling the clamping sleeve toward the base to thereby clamp a cornea between the clamping sleeve and the conical bearing surface. According to another feature, the top end of the clamping sleeve has an outer thread for threadedly engaging with a threaded ring whose upper surface includes a flat guide track for guiding a cutting device, more particularly a keratome.

Advantageously also, a bottom portion of the upper base part and a corresponding portion of the inner wall of the sleeve are made polygonal, e.g. hexagonal, to prevent rotation of the sleeve relative to the upper base part.

According to the invention also, longitudinal slot-like recesses are formed below the thread on the base and can engage resiliently supported elements, preferably balls under spring pressure, which are provided at a corresponding height in the tension ring. The outer surface of the sleeve is formed with longitudinal notch-like slots into which resiliently supported balls can engage. The resiliently supported balls are disposed in two diametrically opposite projections which are formed on the tension ring and project therefrom up to the threaded ring.

BRIEF DESCRIPTION OF THE DRAWINGS

These features and advantages of the present invention as well as others will be more apparent to those skilled in the art when the following description is read in light of the accompanying drawings in which:

The embodiment of the present invention shown in FIGS. 1-4 includes a base 1 including an upstanding base extension having a cylindrical body with a central bore 6. In the base there is a lateral extension communicating with bore 6 and extending to a socket 7 for connection to source of a pressurized medium. The top end of the base extension, which is smaller in diameter than the base, has an outer thread 8 and a central recess 9 for inserting a cylindrical bearing member 3 which, as shown in FIG. 2, has a central bore and a bevelled top edge 10. The top surface of the bearing member 3 forms a cornea support area which conically slopes slightly from the top edge to the central bore. A clamping ring 4 has a central circular opening with a peripheral recess 11 at its bottom edge, whereas the top edge is provided with teeth as shown. The clamping ring 4 is used for tightly clamping a cornea, taken from the donated eye, against the top edge of the cylindrical bearing member 3. The diameter of the opening in the clamping ring is therefore approximately equal to the outer diametrically of the bearing member 3. The clamping ring also has two diametrically opposite, downwardly projecting pins 12 which, as shown in FIG. 1, fit into correspondingly shaped bores 13 formed in the top surface of the base extension. When the pins 12 are fitted in bores 13 the clamping ring cannot shift or twist and the cornea which is to be held fast against shifting or twisting. A tension ring 5, constructed as a union nut, has an inner thread and a central opening approximately equal in diameter to the opening in the clamping ring 4. Two diametrically opposite threaded bores 14 are formed in the edge of the tension ring. Securing or adjusting screws 15 can be screwed into the bores 1C so that their ends projecting from the underside of the tension ring 5 can abut against an anular flange 16 disposed at the tapering top end of the base 1 beneath the threads 8. As shown in FIGS. 2 and 3, the top surface of ring 5 has a central aperture 17 for guiding an inserted microkeratome. The aperture may be bound along parallel sides by dovetailed guides. The cutting device is slideably guided along the guideway during the cutting step. The cutting device for this purpose can be the type disclosed in West German Patent Publication No. 3,147,662.

FIG. 4 diagrammatically shows a cornea 18 inserted into the device of the present invention and clamped between the clamping ring 4 and, the bearing member 3 in the base 1. When a fluid medium is introduced under pressure through socket 7 and bore 6 is applied to the clamped cornea, the cornea curves upwards from the cornea support area of the bearing ring 3 and the space between the bearing member 3 and the cornea fills with the pressurized medium, which can be air or a suitable hydraulic fluid at an adjustable pressure. The pressure on the slice of donated cornea can be measured by conventional means such as an applanation tonometer and adapted to the intraocular pressure measured in the patient's eye. Of course, a continuous measurement can also be made by inserting a pressure-gauge between the chamber cavity and the pressure-source. The pressure-source can be a syringe, tightly connected to the socket 7.

Figure 1C:
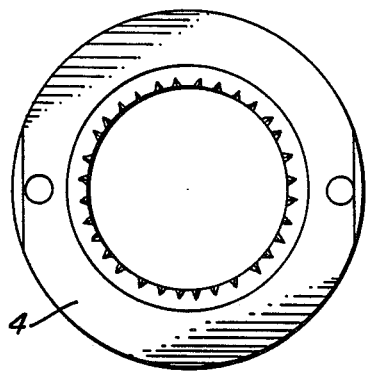
FIGS. 1A, 1B and 1C are plan views of components of the device shown in FIG. 1.
Figure 1B:
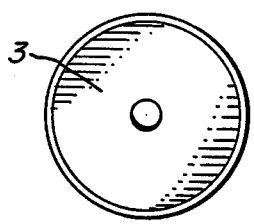
Figure 1A:
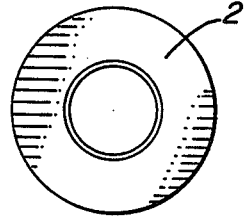
Figure 1:
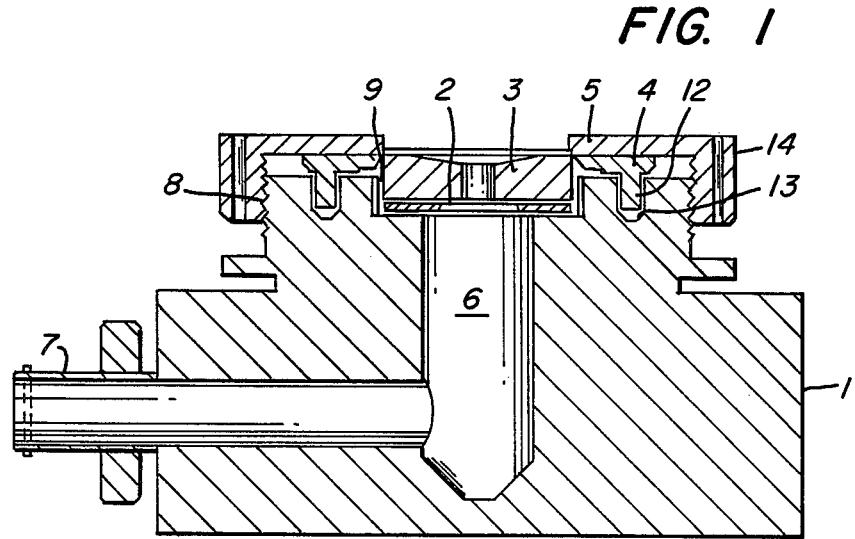
FIG. 1 is a vertical section through one embodiment of the device according to the invention.
Figure 3:
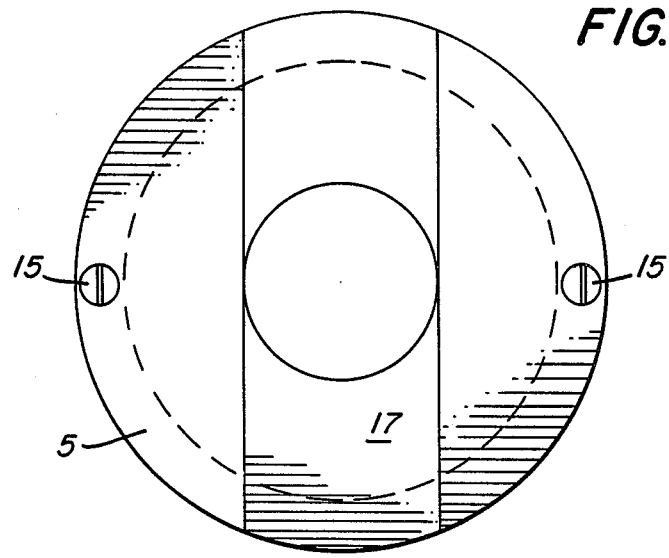
FIG. 3 is a plan view of the tightening screw.
Figure 2:
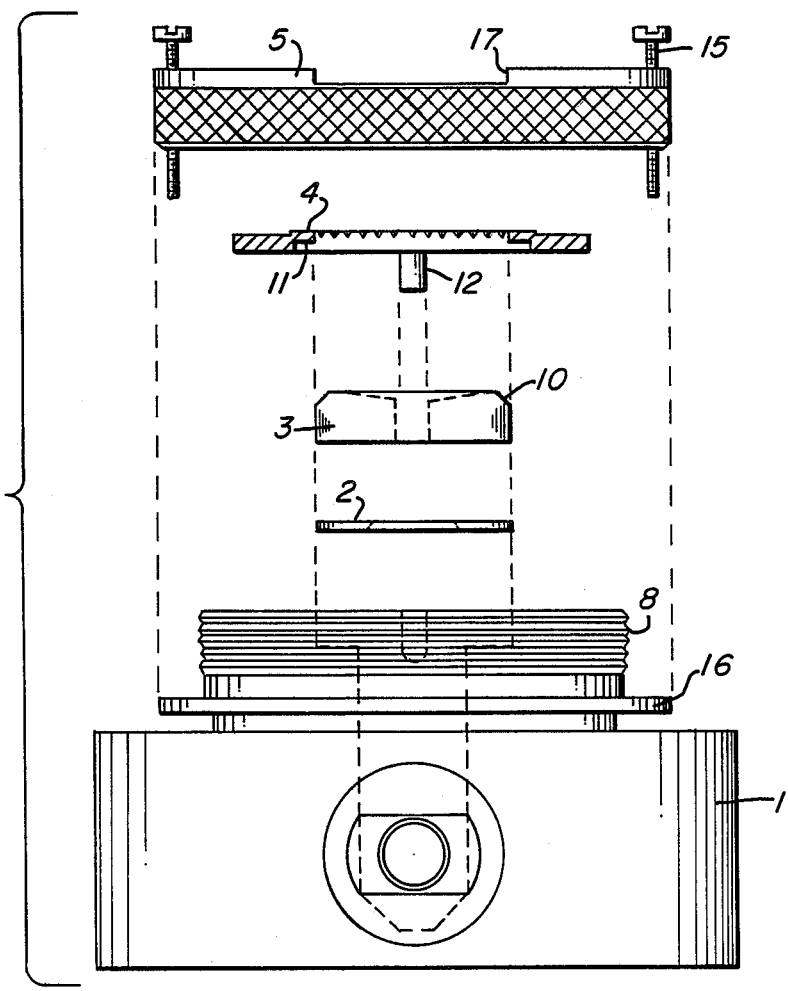
FIG. 2 is a side view of the device shown in FIG. 1, in which the individual components are shown apart and partly in section.
Figure 4:
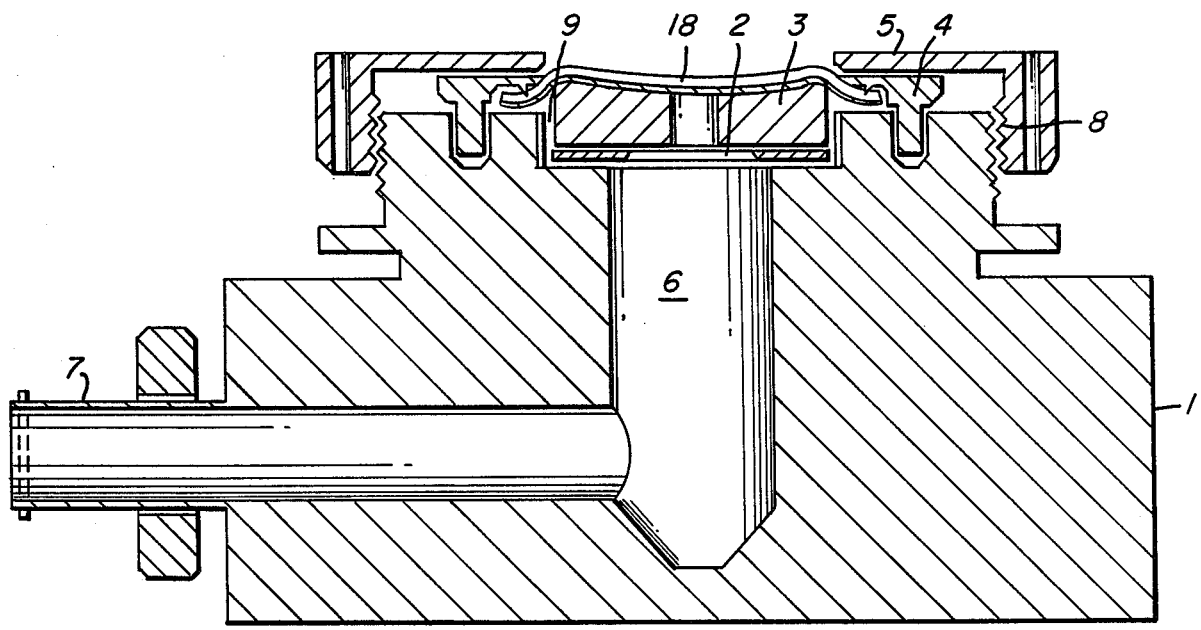
FIG. 4 is an enlarged view of the device shown in FIG. 1, in which a slice of cornea is secured.

According to the present invention, lamellar slices of cornea of varying diameter can be removed by altering the vertical position of the bearing member 3 inside the recess 9. Advantageously to this end, one or more discs 2, which can be of different thicknesses, if required, are inserted between the bearing member and the bottom of recess 9, as shown in FIG. 1.

Figure 5:
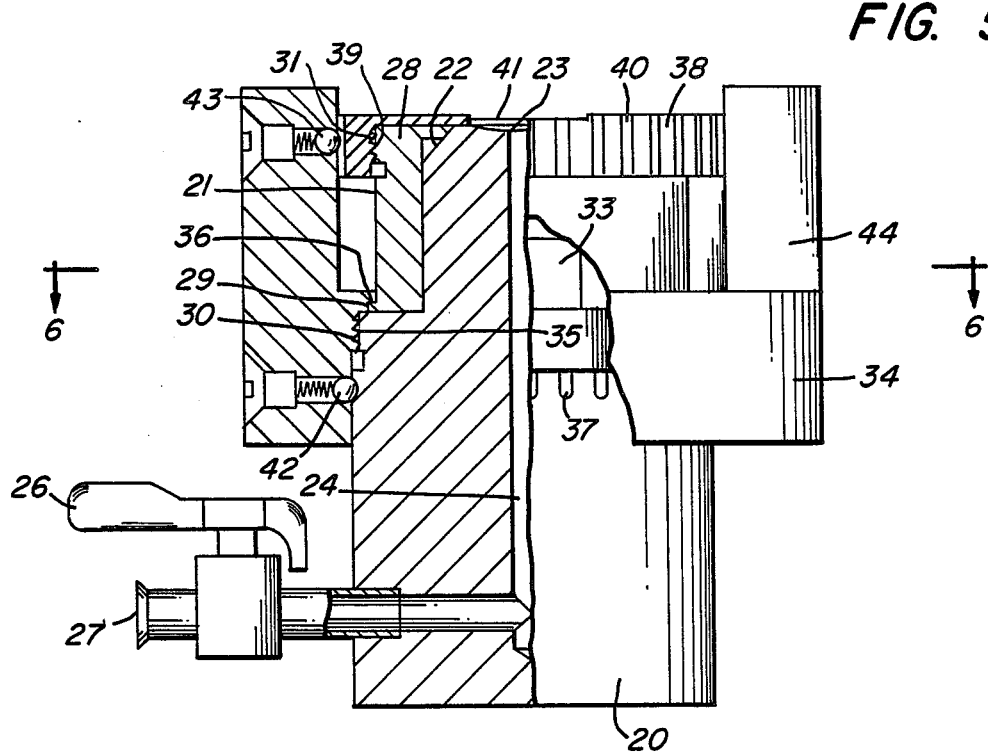
FIG. 5 is a side view, partly in section, of a second embodiment of the invention.
Figure 6:
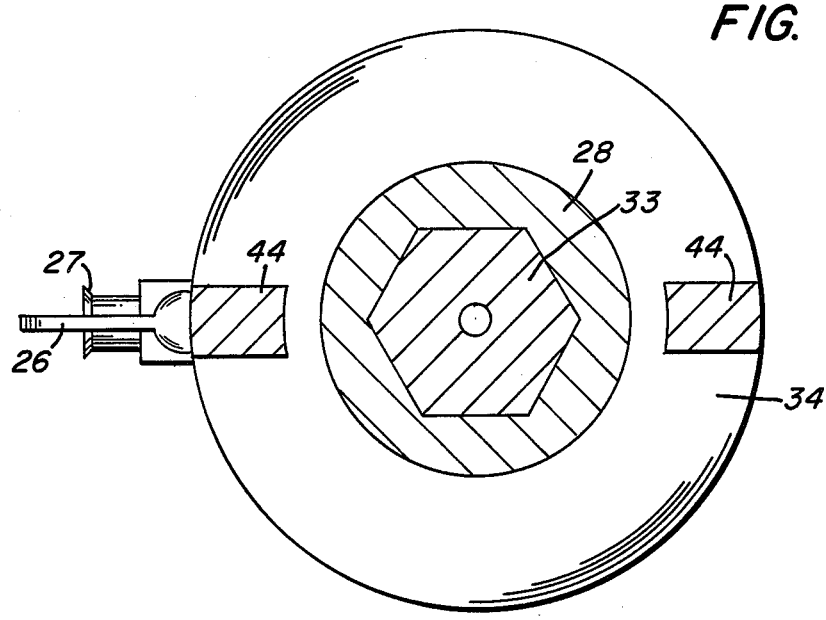
FIG. 6 is a sectional view taken along line A—A of FIG. 5.

FIGS. 5 and 6 show a second embodiment of the present invention in which a base part comprises a cylindrical base 20 and a smaller-diameter upper cylindrical base part 21 integral with the base and preferably made of steel. The upper base part 21 is provided with a conical bearing surface and forming the spigot-like bearing member 22, on which the cornea is placed for processing. The top end face 23 of the bearing member slopes gently from its top edge towards a central bore 24 which extends into the base 20 and extends laterally from the base to a shut-off valve 26 and a socket 27 for connection to a source of pressurized fluid medium. A cornea taken from a donated eye and placed on the end face 23 of member 22 is secured by a sleeve 28 which is positively fitted over the upper cylindrical base part 21. The sleeve 28 has an outer diameter which is smaller than the diameter of base 20. At its bottom end, the sleeve has a outer peripheral flange 29, the outer diameter of which is somewhat smaller than the diameter of external threads 30 at the top end of the base 20. Sleeve 28 also has external threads 31 at its top end; its circular tip opening is somewhat larger than the top edge of the spigot-like bearing member 22, and consequently the edge of the opening abuts the conical portion 23. Advantageously the inner surface surrounding the opening is bevelled-to- match the conical bearing member 22. The sleeve 28 must be prevented from rotating relative to the cylindrical part and, to this end, in the embodiment shown, a bottom portion 33 of the cylindrical part 21 and a corresponding portion of the inner wall of the sleeve 28 are made polygonal, e.g. hexagonal, as shown in FIG. 6. Other methods of preventing relative twisting movement can also be used.

The cornea inserted between the edge of the sleeve opening and the bearing member 22 at the top end of the cylindrical part 21, is tightly clamped by a tension ring 34 having an internal threads 35 for mating with the threads 30 of the base 20. The diameter of the opening at the top of the tension ring 34 is chosen so that the ring can slide over the sleeve 21, but when threadedly engaged with the threads 30, a collar 36 projecting inwardly relative to the threads 35 abuts the flange 29 and, when subsequently tightened, the collar 36 presses flange 29 and sleeve 28 downwards. In this manner, the cornea is tightly clamped between the edge of the sleeve opening and the bevelled portion of the bearing member 22. It has been found advantageous if the outer surface of the base 20 below the threads 30 is formed with longitudinal slot-like recesses 37 which are uniformly distributed around the periphery of the base and cooperate with one or more, preferably two, diametrically opposite resiliently supported members, e.g. balls 42 under spring pressure, which project relative to the inner surface of the tension ring 34 underneath the internal threads 35 in the neighborhood of the slots. This enables the ring to be twisted stepwise into a locked position.

A threaded ring 38 has internal threads 39 for threadedly engaging the threads 31 of the sleeve 28. The diameter of the top opening in ring 38 is approximately equal to the diameter of the top edge of the bearing member 22. A flat guide track 41 is cut diametrically into the top surface of the ring and used for guiding a cutting device, e.g. a keratome, when making the cut. The height of the cut can be set or varied by turning the threaded ring, irrespective of the clamping of the cornea. In order to adjust the ring 38 stepwise, its outer periphery is formed with longitudinal notch-like slots 40 which engage resiliently supported member, e.g. balls 42 under spring pressure, which are disposed in diametrically opposite projections 44 formed on the tension ring 34. The projections 44 extend up to the area of the threaded ring 38.

Although the invention has been shown in connection with certain specific embodiments, it will be readily apparent to those skilled in the art that various changes in form and arrangement of parts can be made to suit requirements without departing from the spirit and scope of the invention.

What I claim is:

1. A device to hold a cornea taken from an eye for processing, said device including the combination of:
   a base including an upstanding base extension having a central bore and an externally threaded section;
   a bearing member including a cornea support area and a central cylindrical bore supported by said upstanding base extension,
   a clamping ring including means for preventing rotation thereof while loosely resting about said bearing member for pressing a cornea for processing against said bearing member,
   a tension ring threadedly engaged with the externally threaded section of said base for relative rotation to establish thereby the contact pressure on a cornea by pressing the cornea between said clamping ring and said bearing member, said
   means for delivering a pressure medium to the central bore of said base.

2. The device according to claim 1 wherein said bearing member includes a base surface which is concave and extends from said central bore to an outer bevelled edge portion.

3. The device according to claim 2 wherein said clamping ring includes cornea griping surfaces to engage with an outer peripheral edge portion of the cornea to press the cornea against said outer bevelled edge portion of the bearing member.

4. The device according to claim 3 wherein said cornea gripping surfaces comprise gripper teeth.

5. The device according to claim 4 wherein said cornea gripping surfaces comprise sharp member sections.

6. The device according to claim 1 wherein said means for preventing rotation of said clamping ring includes pin sections extending at uniformly spaced apart locations about the periphery of the clamping ring for engagement in bores formed in said upstanding base section when the clamping ring is placed on the outer edge of the bearing member.

7. The device according to claim 1 wherein said base includes a flange surface and wherein said tension ring has diametrically opposite threaded bores and wherein said device further includes two bolt members each having a threaded portion to engage with the threads of one of said threaded bore while an end portion of the bolt member abuts against said flange surface.

8. The device according to claim 1 further including disc means between said base extension and said bearing member to establish a predetermined distance between the bearing member and base extending.

9. The device according to claim 8 wherein said disc means includes an annular disc which fits into a central recess on said base extension.

10. The device according to claim 1 further including means carried by said tension ring for guiding a microkeratome to traverse across a cornea while supported on said bearing member.

11. The device according to claim 10 wherein said means for guiding includes a guide track carried by said tension ring.

12. A device to hold a cornea taken from an eye processing, said device including the combination of:
a base including an upper base part having a conical bearing surface at the projected end of said upper base part for supporting a cornea,
a clamping sleeve fitted on an outer surface area of said upper base part, said clamping sleeve including an outer peripheral flange; and
a tension ring threadedly engaged with said upper base part and engaged with said peripheral flange for relative rotation to establish thereby the contact pressure on a cornea by pulling said clamping sleeve toward said base to thereby clamp a cornea between said clamping sleeve and said control bearing surface.

13. The device according to claim 12 further including a threaded ring threadedly engaged with said clamping sleeve, and means carried by said threaded ring for guiding a cutting device to traverse across a cornea while supported by said conical bearing surface.

14. The device according to claim 13 wherein said means carried by said threaded ring for guiding includes a guide track carried by said threaded ring.

15. The device according to claim 14 wherein said guide track is flat for guiding a keratome.

16. The device according to claim 12 wherein said upper base part and said clamping sleeve include a polygonal surfaces for preventing relative rotation by interlocking engagement.

17. The device according to claim 16 wherein said polygonal surfaces are hexagonal surfaces.

18. The device according to claim 12 further including detent means resiliently supported by said tension ring to engage with recesses in said base for preventing relative rotation therebetween.

19. The device according to claim 18 wherein said detent means includes balls.

20. The device according to claim 12 wherein said tension ring includes upstanding projections at diametric opposite sides of said base part, said device further including detent means resiliently supported by said upstanding projections to engage with recesses in said base for preventing relative rotation therebetween.

21. The device according to claim 20 wherein said recesses in said base comprise notch-like recesses and wherein said detent means comprise balls urged by springs toward said notch-like recesses.

22. The device according to claim 12 further including means for delivering a pressure medium including a passageway in said bore extending to said conical bearing surface.

* * * * *